United States Patent [19]

Melgaard

[11] Patent Number: 4,846,669
[45] Date of Patent: Jul. 11, 1989

[54] CONTINUOUS MATERIAL HEATING OVEN

[75] Inventor: Hans L. Melgaard, Minneapolis, Minn.

[73] Assignee: Despatch Industries, Inc., Minneapolis, Minn.

[21] Appl. No.: 193,836

[22] Filed: May 13, 1988

[51] Int. Cl.[4] .............................................. F27B 9/28
[52] U.S. Cl. ........................................ 432/59; 432/72; 432/152
[58] Field of Search ..................... 432/59, 8, 72, 144, 432/152

[56] References Cited

U.S. PATENT DOCUMENTS

| | | | |
|---|---|---|---|
| 2,750,680 | 6/1956 | Houndry et al. | 432/72 |
| 3,437,422 | 4/1969 | Guckel . | |
| 3,899,862 | 8/1973 | Muys et al. . | |
| 3,977,091 | 8/1976 | Hortig et al. . | |
| 4,115,052 | 9/1978 | Flynn | 432/72 |
| 4,140,479 | 2/1979 | Sirch et al. . | |
| 4,217,090 | 8/1980 | Whike et al | 432/72 |
| 4,349,508 | 9/1982 | Liede . | |
| 4,518,353 | 5/1985 | Banno et al. | 432/152 |
| 4,573,909 | 3/1986 | Scanlon | 432/152 |
| 4,588,378 | 5/1986 | Yamamoto et al. | 432/152 |
| 4,597;192 | 7/1986 | Sfondrini et al. . | |
| 4,681,616 | 7/1987 | McMaster | 432/152 |
| 4,767,320 | 8/1988 | Sasaki et al. | 432/152 |

Primary Examiner—Henry C. Yuen
Attorney, Agent, or Firm—James R. Haller

[57] ABSTRACT

The invention relates to a continuous material heating oven ideally suited for sterilizing and depyrogenating materials for introduction to a sterile environment. The oven includes a cool air supply means which is self-deprogenating eliminating the need for manual sterilization. A volumetric airflow control means is included with the cool air supply means for substantially linearly cooling materials to reduce breakage. Control means is provided by the system for maintaining the sterile environment at a greater positive pressure than its adjacent environments to protect the sterile environment from contamination.

9 Claims, 2 Drawing Sheets

CONTINUOUS MATERIAL HEATING OVEN

FIELD OF THE INVENTION

The invention relates to material heating equipment and, more particularly to a continuous material heating oven that may be used for continuously depyrogenating, sterilizing, drying, and critical finish drying materials for introduction to a sterile environment such as a clean room.

BACKGROUND OF THE INVENTION

Material heating ovens of the past such as depyrogenation ovens have required frequent, highly labor intensive cleaning of cooling systems in order to sterilize them for use. One of the cleaning methods commonly employed involves manually wiping the interior surfaces with a sterilizing agent to remove unwanted particulate matter. It is difficult if not impossible to remove all undesirable particulate matter using this method. Another method of cleaning ovens involves fogging the interior of the oven with a sterilizing agent.

Ovens used for heating objects such as glassware often have cooling systems which cool glassware too rapidly, causing breakage to occur. These ovens generally do not have the capability to cool materials in a precisely controlled manner.

Pressure control systems are commonly used in conjunction with material heating ovens to maintain sterile environments at greater positive pressures than the adjacent environments. This pressure differential functions to maintain airflow, if any, in a direction away from the sterile environment towards the surrounding generally particle laden environment so that impurities do not enter the former environment.

It would be desirable to have a material heating oven including a sterilizing system which eliminates manual sterilization of the oven before start-up, which may include a controlled cooling system for preventing glassware breakage, and which may include a controlled pressurization system for maintaining cleanliness in a sterile environment.

SUMMARY OF THE INVENTION

The continuous material heating oven of the invention may be used for the depyrogenation and sterilization of materials and employs a self-sterilizing cool air supply for providing cooled air to an oven tunnel to cool materials contained therein. A heating means is included in the cool air supply portion to heat it to a temperature suitable for depyrogenation and sterilization to rid it of bacteria and other particulate matter. The heating means eliminates the need to sterilize the cool air supply portion by conventional methods (e.g., manually wiping or fogging with a sterilizing agent) which tend to be less than sufficiently effective in removing undesirable particulate matter.

The cool air supply portion of the oven further includes linearized cooling means for approximate linear cooling of objects after they have been heated to an elevated temperature. A perforated plate desirably is utilized to supply cooled air in a controlled manner to hot objects to reduce thermal stress and breakage.

The invention in a further embodiment comprises pressure differential control means carried between the sterile environment and the cool air supply portion for maintaining the sterile environment at a greater positive pressure with respect to the cool air supply portion. The pressure differential functions to maintain flow of air in a direction from the sterile environment to the oven or other environment to prevent dirty air from entering and contaminating the sterile environment.

DETAILED DESCRIPTION OF THE PREFERRED EMBODIMENTS

Figure 1:
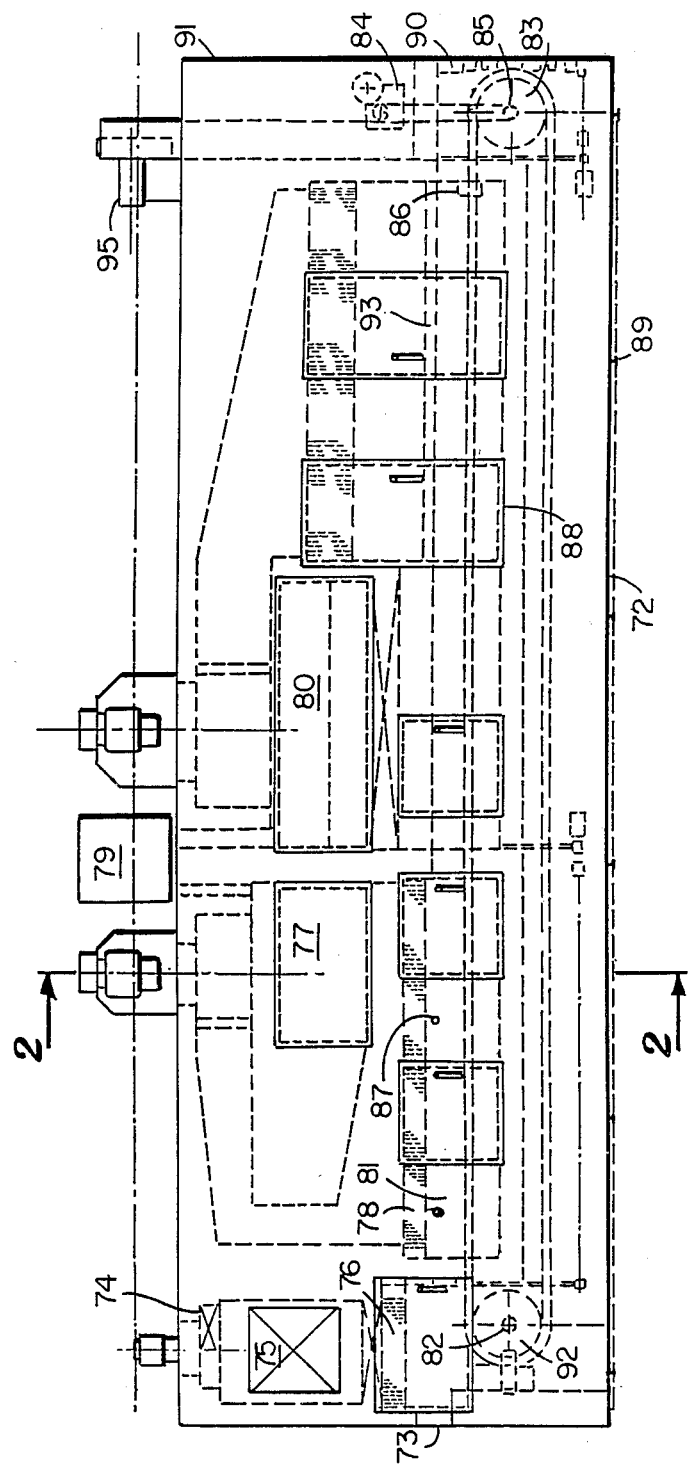
FIG. 1 is an elevational view of the continuous material heating oven of the invention.
Figure 2:
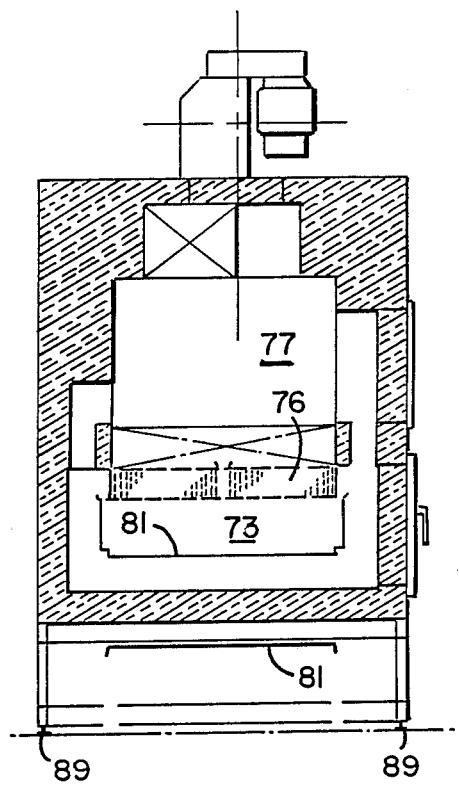
FIG. 2 is a cross-sectional view of the oven of FIG. 1 taken along line 2—2 thereof.

The continuous material heating oven shown in FIGS. 1 and 2 as 72 enables materials to be sterilized and depyrogenated for introduction into a sterile environment in a continuous manner. Referring to FIG. 1, the continuous material heating oven 72 comprises an airwash portion 74, a hot air supply portion 77, and a cool air supply portion 80. Materials to be sterilized are introduced into an oven tunnel 73 onto an elongated conveyor belt 81 that extends through the length of the oven 72 to a sterile environment. The process portions of the oven are arranged sequentially with the airwash portion being carried adjacent the entrance to the tunnel 73, the hot air supply portion 77 next adjacent, and the cool air supply portion 80 carried adjacent the sterile environment.

The airwash portion 74 comprises a prefilter 75, a filter 76, air moving means (e.g., a blower) and a plurality of air jets which direct airstreams downwardly onto glassware and other objects carried by the conveyor belt 81 to remove loose particles.

After the airwash 74, the objects are conveyed into the hot air supply portion 77 where they are heated to a suitable depyrogenation temperature. Hot air, suitably filtered, may be supplied to the oven tunnel 73 by the hot air supply portion 77, shown in the cross-sectional view of FIG. 2. The air flow in the hot air supply portion 77 is preferably in a downwardly direction to remove any particulate matter from the glassware in a downwardly direction. Preferably the hot air supply portion 77 is maintained at an operating temperature of approximately 350° C., which is a suitable temperature for depyrogenation. The hot air supply portion 77 includes a filter 78 to remove particles greater than a predetermined particle size. After heating, the objects are conveyed further by the belt 81 into the cool air supply portion 80 of the oven 72.

The cool air supply portion 80, separated from the hot air supply portion 77 by a partial divider having an opening for a blower and a filter and includes an air heating device for heating the cool air supply to a suitable sterilization temperature prior to its use for cooling the oven tunnel 73. The cool air supply 80 functions to supply cool, filtered air to the oven tunnel 73. In the cooling portion 80, cool air is passed downwardly through a perforated plate 93 toward the objects carried by the belt 81. Preferably carried in a generally horizontal plane above the conveyor belt 81, the perforated plate 93 includes a plurality of differently sized openings through its thickness. Preferably, the openings 93 adjacent the entrance to the cooling portion have small diameters which enable only a small volume of air to pass through. The openings in the middle portion of the perforated plate 93 are preferably larger to allow a slightly greater volume of air to pass through. The opposite end of the perforated plate may contain openings with a generally larger diameter than the openings in the middle portion to allow a larger volume of air to pass through.

The perforated plate enables a small volume of cool air to initially contact the hot glassware entering the cooling portion and increasingly larger volumes of air to be applied to the glassware as it progresses through the cooling portion. In this manner the glassware may be substantially linearly cooled (e.g., a plot of temperature vs. time of glassware moving through the cooler is approximately linear within a specified temperature range), which reduces or eliminates glassware breakage due to thermal stress. Approximately linear is meant to convey that from a straight line joining points of the plot at the extremes of a specified temperature range, the points falling between the extreme points will correspond to temperatures within 20% of the line. The temperature range over which linearity of the cooling curve is most important is generally between 200° C. and 350° C. This is the range within which heated objects, particularly glassware, are most susceptible to stress cracking. Maintaining the cooling curve approximately linear in this region reduces stress cracking and breakage of glassware. It should be understood that the perforated plate 93 and the openings contained thereupon could be any of a number of shapes and sizes and the plate 93 is not limited to a planar configuration. The perforations in the plate 93 may be arranged as previously described or alternatively in progressively larger diameters along the length of the plate from the entrance to the exit of the cooler. The air pressure above the perforated plate 93 is preferably maintained uniform across the surface of the plate The flow direction of the air in the cooling portion is preferably generally downwardly to carry any particles downwardly away from the materials carried by the conveyor belt 81. The belt 81 preferably includes openings to allow air to pass downwardly through it to facilitate substantially laminar or "plug" flow of air throughout the oven tunnel 73 to avoid significant air turbulence. Air turbulence is undesirable in the oven tunnel because it may stir up particulate matter and deposit it onto objects carried by the belt 81.

After cooling, the glassware and other materials are transported through a small opening in the wall 91 into a sterile environment. The wall 91 preferably comprises an air-tight material which is carried between the sterile environment and the oven to prevent impurities and other particulate matter from entering the sterile environment. A photo eye 86 is preferably employed to detect materials extending above the lip of the belt 81. The photo eye 86 is used to open an adjustable profile plate 90 when a first row of materials carried by the belt 81 reach it. The profile plate 90 remains open until the system is shut down. The adjustable profile plate 90 is carried between the cool air supply portion 80 and the sterile environment for adjustably varying the open area at the end of the tunnel to minimize the open area while allowing for size variation of the materials passing therethrough.

A pressure differential is maintained across the wall, the sterile environment being maintained at a greater positive pressure than the cool air supply device 80 carried by the oven. In a preferred embodiment, the pressure differential is maintained by a pressure control system comprising commercially available a PID (proportional, integral and derivative) electronic controller having pressure sensing transducers carried in the cool air supply device 80, the sterile environment, and the room in which the oven is contained. Preferably, the pressure maintained within at least a portion of the cool air supply device 80 is less than the average of the pressures of the sterile environment and the room in which the oven is contained. This pressure differential is maintained to prevent air flow from the cool air supply device 80 and other areas into the sterile environment. A variable speed blower 95, operatively controlled by the PID controller, is used to exhaust air from the cool air supply device 80 to aid in controlling the pressure within the device. Any airflow through the wall 91 between the two environments will be in the direction away from the sterile environment due to the pressure differential. Preferably, the pressure sensing transducer in the cool air supply portion 80 and the exhaust blower are positioned near the material exit end so that the same end may be maintained at a pressure approximately equal to the average of the pressures maintained by the sterile environment and the room environment. The remainder of the cool air supply 80 includes a pressure differential, the interface between the hot air supply portion 77 and the cool air supply portion 80 being held at substantially the same pressure as the room environment. It is desirable also to maintain the interfaces between the hot air supply 77, the air wash 74 and the room environment (in which the oven is contained) at a pressure differential of approximately zero. The zero pressure differential may prevent hot air from entering the airwash portion from the hot air supply device which could cause damage to portions of the airwash system.

The continuous material heating oven 72 preferably includes a plurality of strategically located particle count ports 87 to enable a user to measure particle counts along the length of the oven. These ports 87 preferably extend through the outside wall of the oven housing, providing unconstrained accessibility to various portions of the oven.

A plurality of access doors 88 are preferably provided in side walls of the oven 72, allowing a user access to the inside of various portions of the oven including the tunnel 73, the airwash portion 74, the hot air supply portion 77, and the cool air supply portion 80.

The oven preferably includes HEPA filters carried by the airwash, hot air supply and cool air supply portions through which air is passed prior to entering the oven tunnel 73. Additionally, a prefilter 79 may be carried by the outside air intake to the hot air supply portion and the cool air supply portion to prefilter the air that is drawn into these portions.

The conveyor belt assembly may include an air take-up assembly 92 containing a rack and gear for maintaining tension on the belt while allowing for expansion.

The conveyor 81 employed to move objects through the oven tunnel 73 and into the sterile environment may extend from the entrance of the tunnel 73 to the unloading end of the tunnel. In a preferred embodiment, the conveyor 81 comprises a belt of woven stainless steel or other suitable material having upturned lateral edges to prevent materials from falling off of the sides. The belt is carried generally horizontally and extends around two cylinders 82,83 carried by opposite ends of the tunnel 73. It is powered by an electric motor, and includes a drive assembly 84 (preferably of the type incorporating a variable speed drive), a gear reducer, roller chain, roller gears, and a torque limiter. The cylinder shaft 83 of the belt preferably includes a shaft encoder 85 to measure the speed of the belt.

A plurality of adjustable support legs 89 are carried by the underside of the system to support the system above the surface of the floor and to enable the height of the system to be adjusted to level the system.

While a preferred embodiment of the present invention has been described, it should be understood that various changes, adaptations and modifications may be made therein without departing from the spirit of the invention and the scope of the appended claims.

What is claimed is:

1. An oven for continuously sterilizing objects comprising
    means defining an elongated oven cavity having an entrance and an exit,
    conveyor means for carrying objects to be sterilized from the entrance of the oven cavity to the exit,
    hot air supply means for supplying hot air to a portion of the oven cavity,
    cool air supply means for supplying cooled air to a second portion of the oven cavity adjacent the exit, and
    means for varying the volumetric flow rate of said cool air supplied to the objects in said second portion so that a lesser volume of cool air is supplied to the objects upon entrance to the second portion and a progressively greater volume of air is supplied to the objects as they progress through the second portion, thus cooling the objects at a substantially linear cooling rate within a predetermined temperature range to avoid thermal shock to the objects being sterilized.

2. The oven of claim 1 including pressure control means for maintaining a positive pressure within the cooling portion of the oven cavity near its exit at a level below that of a sterile environment into which sterilized, cooled objects are transported from the cooling portion of the oven.

3. The oven of claim 1 including an air heating means carried by the cool air supply means for heating the cool air supply means to an elevated temperature suitable for sterilizing and depyrogenating the same prior to using the device to supply cool air to the oven cavity.

4. The material heating oven of claim 2 wherein the pressure control means includes an electronic PID controller and a plurality of pressure sensing transducers for detecting gage pressure in selected portions of the oven, the controller maintaining a pressure differential between the sterile environment, the cool air supply means, and the environment surrounding the oven, the sterile environment being maintained at a greater positive pressure than the cool air supply means.

5. The material heating oven of claim 1 wherein the means for varying the flow rate of cooled air comprises a perforated plate carried generally horizontally above the conveyor means, the plate having numerous sizes of perforations extending through its thickness.

6. The material heating oven of claim 5 wherein the perforations are arranged in groups of like size, several groups of perforations of increasing diameter being carried adjacent one another throughout the length of the plate.

7. The oven of claim 1 wherein said cool air supplied to the objects in said second portion is directed downwardly normal to the direction of flow of objects through the oven.

8. The oven of claim 1 wherein the flow of hot air and cool air supplied to the objects is substantially laminar.

9. A material heating oven for continuously sterilizing and providing items to a sterile environment comprising,
    (a) an elongated oven tunnel;
    (b) hot air supply means for supplying heated air to the oven tunnel;
    (c) cool air supply means for supplying cool air to the oven tunnel to cool the items carried within;
    (d) an air heating device carried by the cool air supply means for heating and sterilizing the same;
    (e) volumetric airflow control means carried by the cool air supply means for regulating the volume of cool air supplied to the items carried within the oven tunnel, the volumetric airflow control means comprising a perforated plate carried generally horizontally above the conveying means, the plate having numerous sizes of perforations extending through its thickness to provide a substantially linear cooling rate within a predetermined temperature range to avoid thermally stressing objects being sterilized;
    (f) pressure control means comprising an electronic PID controller and a plurality of pressure sensing transducers for maintaining a pressure differential between the sterile environment, the cool air supply means, and the environment surrounding the oven, the sterile environment being maintained at a greater positive pressure than the cool air supply means to prevent contamination of the sterile environment; and
    (g) conveyor means for carrying objects to the sterilized through the oven tunnel in a continuous manner.

* * * * *

UNITED STATES PATENT AND TRADEMARK OFFICE
CERTIFICATE OF CORRECTION

PATENT NO. : 4,846,669

DATED : July 11, 1989

INVENTOR(S) : Hans L. Melgaard

It is certified that error appears in the above-identified patent and that said Letters Patent is hereby corrected as shown below:

On the title page:

In the Abstract, fifth line, first word, replace "deprogenating" with --depyrogenating--.

Column 2, line 53, between the words "for" and "a", insert --materials to pass therethrough, comprises an air cooling means,--.

Signed and Sealed this

Twenty-second Day of May, 1990

Attest:

HARRY F. MANBECK, JR.

*Attesting Officer*   *Commissioner of Patents and Trademarks*